US00PP19966P2

(12) United States Plant Patent
Cornelis

(10) Patent No.: US PP19,966 P2
(45) Date of Patent: Apr. 28, 2009

(54) ***SPATHIPHYLLUM* PLANT NAMED 'ZOE'**

(50) Latin Name: *Spathiphyllum Schott*
Varietal Denomination: ZOE

(76) Inventor: Daniel Cornelis, Oude Gaverweg 2, Melsen-Merelbeke (BE), 9820

( * ) Notice: Subject to any disclaimer, the term of this patent is extended or adjusted under 35 U.S.C. 154(b) by 0 days.

(21) Appl. No.: 12/079,636

(22) Filed: Mar. 27, 2008

(51) Int. Cl.
*A01H 5/00* (2006.01)

(52) U.S. Cl. ..... Plt./364
(58) Field of Classification Search ..... Plt./364
See application file for complete search history.

*Primary Examiner*—Annette H Para

(57) ABSTRACT

A new and distinct *Spathiphyllum* cultivar named 'ZOE' is disclosed, characterized by dark green, glossy foliage, strong, bushy basal emergence of leaves and clear white inflorescence with a slight green vein. The new variety is commercially suitable for indoor plant production.

1 Drawing Sheet

Figure 1:
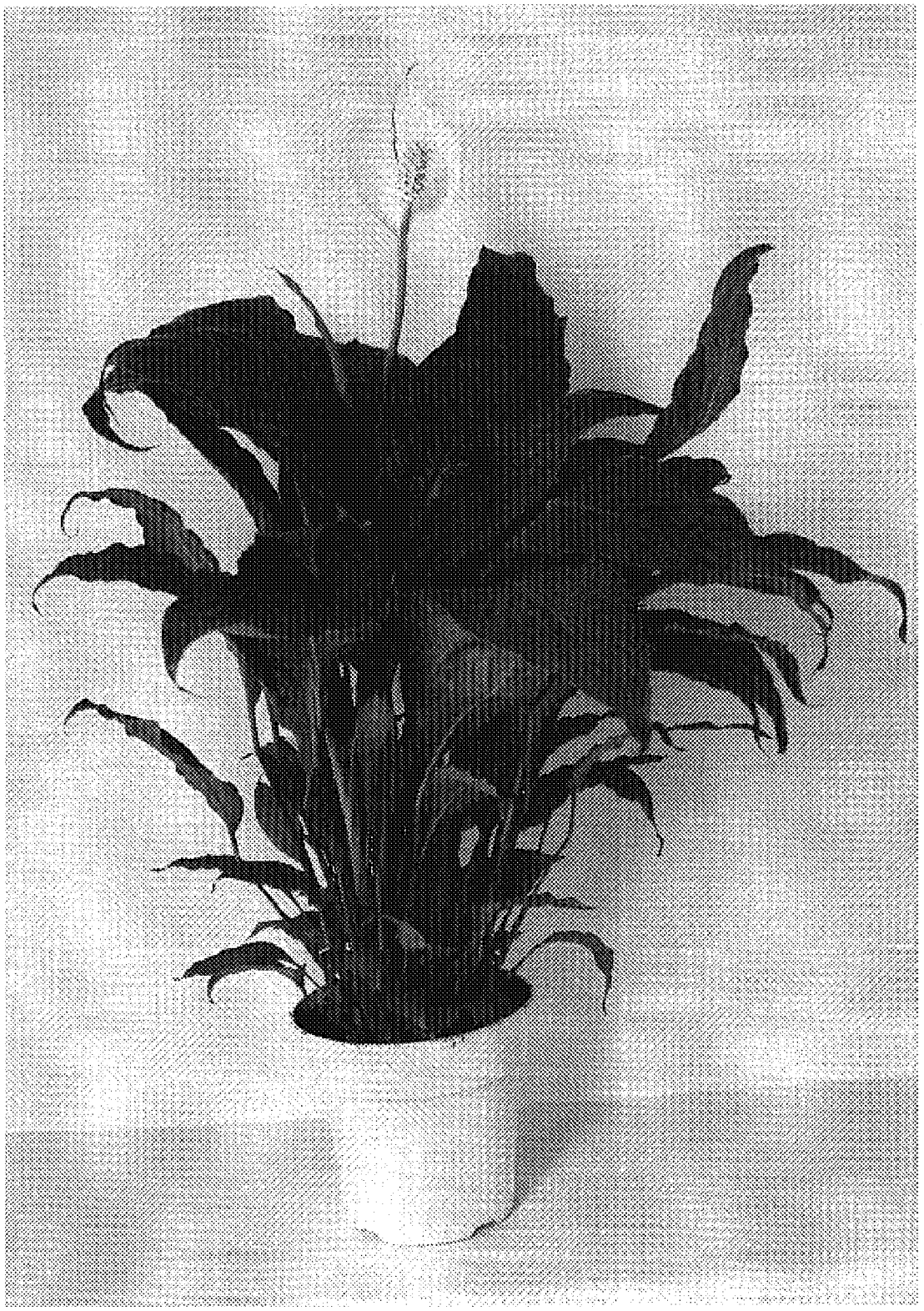

Latin name of the genus and species: *Spathiphyllum Schott.*
Variety denomination: 'ZOE'.

BACKGROUND OF THE INVENTION

The new cultivar is a product of a planned breeding program. The new variety originated from a cross pollination, made by the inventor, of an unidentified, unpatented seed parent and an unidentified, unpatented pollen parent, both *Spathiphyllum Schott.*

The new variety was discovered by the inventor, Daniel Cornelis, a citizen of Belgium, in February 2003 in a group of seedlings resulting from the crossing. The new cultivar was found in a commercial green house belonging to the inventor in Melsem-Merelbeke, Belgium.

Asexual reproduction of the new cultivar 'ZOE' was first performed in Belgium by tissue culture in May 2004. 'ZOE' has been reproduced by micro-propagation and has shown that the unique features of this cultivar are stable and reproduced true to type. At least 6 generations have been reproduced at the time of this filing.

SUMMARY OF THE INVENTION

The cultivar 'ZOE' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'ZOE.' These characteristics in combination distinguish 'ZOE' as a new and distinct *Spathiphyllum* cultivar:

1. Dark green foliage.
2. Glossy foliage.
3. Clear white inflorescence.
4. Distinctive bushy base due to a high number of shoots arising from the base of the plant.

Plants of the new cultivar 'ZOE' cannot be compared to either seed parent or pollen parent as records of those characteristics were not kept. However, 'ZOE' can be compared to the commercial variety *Spathiphyllum Schott.* 'Mara' U.S. Plant Pat. No. 16,422. Plants of 'Mara' are similar to plants of 'ZOE' in most horticultural characteristics, however, 'ZOE' has much darker and smaller leaves than 'Mara.' Additionally 'ZOE' produces many more shoots and has a smaller inflorescence than 'Mara.'

'ZOE' can also be compared to compared to the commercial variety *Spathiphyllum Schott.* 'Alfa CD' U.S. Plant Pat. No. 10,823. Plants of 'Alfa CD' are similar to plants of 'ZOE' in most horticultural characteristics, however, 'ZOE' has much darker and glossier leaves than 'Alfa CD.' Additionally 'ZOE' produces many more shoots and has more crenated leaf margins than 'Alfa CD.'

BRIEF DESCRIPTION OF THE PHOTOGRAPH

The accompanying photograph in FIG. 1 illustrates in full color a typical plant of 'ZOE' grown in a greenhouse in Apopka, Fla. This plant is approximately 9 months old, shown in a 6 inch pot. The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart except where general terms of ordinary dictionary significance are used. The following observations and measurements describe 'ZOE' plants grown in a climate controlled greenhouse in Apopka, Fla., USA. Temperatures ranged from 18° C. to 22° C. at night to 18° C. to 22° C. during the day. No artificial light, photoperiodic treatments or chemical treatments were given to the plants. Measurements and numerical values represent averages of typical plant types.

Botanical classification: *Spathiphyllum Schott.* cultivar 'ZOE.'

PROPAGATION

Time to initiate roots: Approximately 8 days from an initial cutting at approximately 20 to 22° C.

Time to produce rooted cutting: Approximately 16 days at approximately 20 to 22° C.
Root description: Fine, fibrous.

PLANT

Growth habit: Leaves growing directly from base of plant, with no stems.
Plant shape: Upright, leaves slightly arching out.
Height: Approximately 48 cm.
Plant spread: Approximately 32 cm in a 6 inch pot.
Normal pot size: 6 inch and larger.
Growth Rate: Moderate.
Branching characteristics: No branching. Leaves emerge direct from base of plant.
Number of clumps of leaves: 12.
Number of leaves per Clump: Average 15.
Number of leaves per plant: Approximately 180.
Age of plant described: Approximately 9 months.

FOLIAGE

Leaf:
*Arrangement.*—Single leaves emerging basally.
*Average length* (*excluding petiole*).—Approximately 22.5 cm.
*Average width.*—Approximately 9.8 cm.
*Shape of blade.*—Elliptic.
*Aspect.*—Slightly recurved.
*Apex.*—Apiculate.
*Base.*—Attenuate.
*Margin.*—Entire.
*Texture of top surface.*—Smooth, moderately glossy.
*Texture of bottom surface.*—Smooth, moderately glossy.
*Color.*—Young foliage upper side: Near R.H.S. Green 139B. Young foliage under side: Near R.H.S. Green 137D. Mature foliage upper side: Near R.H.S. Green 139A. Mature foliage under side: Near R.H.S. Green 141C.
Venation:
*Type.*—Pinnate.
*Venation coloration upper side.*—Green 143A.
*Venation coloration under side.*—Green 143C.
Petiole (excluding Geniculum):
*Length.*—Approximately 23 cm.
*Width.*—At geniculum: Approximately 0.6 cm. Above clump: Approximately 1.1 cm.
*Color.*—Near RHS Green 141C.
*Strength.*—Moderate.
Geniculum:
*Length.*—Approximately 3.2 cm.
*Width.*—Approximately 0.6 cm.
*Color.*—Near RHS Green 143B.

INFLORESCENCE

*Arrangement.*—Spathes with spadices held above the foliage on erect peduncles arising from the petiole sheath.
*Flowering habit.*—Continuous.
*Quantity of spathes per plant.*—On average 3 fully open spathes in good condition.
*Natural flowering season.*—Autumn to Winter.
*Time of flowering.*—6 months.
*Fragrance.*—Very slight. Sweet.
*Self-cleaning or persistent.*—Persistent.
*Flower longevity.*—Flowers stay in good condition approximately 3 weeks on the plant.
Spathe:
*Aspect.*—Slightly concave. More concave at base, mostly flat moving towards apex.
*Length.*—Approximately 14 cm.
*Width.*—Approximately 5.6 cm.
*Shape.*—Elliptic.
*Margin.*—Entire.
*Apex.*—Apiculate, with a slight twist.
*Base.*—Cuneate.
*Color.*—Front when opening: Near RHS White 155C. Strong mid-vein and some small lateral veins of RHS Green 141C and 141D. Back when opening: Near RHS White 155C. Strong mid-vein and some small lateral veins of RHS Green 141C and 141D. Front when mature: Near RHS White 155C. Strong mid-vein and some small lateral veins of RHS Green 141C and 141D. Back when mature: Near RHS White 155C. Strong mid-vein and some small lateral veins of RHS Green 141C and 141D. Fading to: No fading
Spadix
*Shape.*—Columnar, arising from the top of the peduncle.
*Tip.*—Obtuse.
*Base.*—Obtuse.
*Length.*—Approximately 4.5 cm.
*Width.*—Approximately 2.8 cm.
*Color.*—When opening: Near RHS Yellow-White 158C.
*Mature.*—Near RHS Yellow-White 158B.
*Quantity of flowers per spadix.*—Approximately 130.
*Spadix flower arrangement.*—Bisexual, rounded.
*Spadix flower diameter.*—Approximately 0.2 cm.
*Spadix flower depth.*—Approximately 0.1 cm.
Peduncle:
*Length.*—Approximately 35 cm.
*Width.*—Approximately 0.8 cm.
*Color.*—Near RHS Green 141C.
*Strength.*—Moderate.

REPRODUCTIVE ORGANS

*Ovary color.*—Near RHS 155B.
*Stigma color.*—Near RHS 155B.
*Anther color.*—Near RHS 155A.
*Quantity of pollen.*—Scant.
*Pollen color.*—Near RHS 155A.

OTHER CHARACTERISTICS

Disease resistance: Neither resistance nor susceptibility to diseases or pests has been observed in this variety.
Drought tolerance and cold tolerance: The new cultivar is a typical *Spathiphyllum*, cold tolerant to approximately 5 to 7° C. and does not tolerate drought.
Fruit/seed production: Not observed.

What is claimed is:

1. A new and distinct cultivar of *Spathiphyllum* plant named 'ZOE' as herein illustrated and described.

* * * * *